United States Patent [19]

Winchell et al.

[11] 4,176,173

[45] Nov. 27, 1979

[54] RADIOGRAPHIC COMPOSITIONS

[75] Inventors: Harry S. Winchell, Lafayette; Tz-Hong Lin, Fremont; Charles A. Panneciere, Alemeda, all of Calif.

[73] Assignee: Medi-Physics, Inc., Emeryville, Calif.

[21] Appl. No.: 816,618

[22] Filed: Jul. 18, 1977

[51] Int. Cl.$^2$ ............................................. A61K 29/02
[52] U.S. Cl. ............................................. 424/5; 424/4
[58] Field of Search ................... 424/4, 5; 260/429 J, 260/429.3, 343.7

[56] References Cited

U.S. PATENT DOCUMENTS

| | | | |
|---|---|---|---|
| 3,137,717 | 6/1964 | Peters | 260/429.3 |
| 3,198,817 | 8/1965 | Langer | 260/429.3 |
| 3,553,316 | 1/1971 | Rubino | 260/429 J |
| 3,937,800 | 2/1976 | Dure-Smith et al. | 424/4 |
| 4,020,091 | 4/1977 | Budnick | 260/429.3 |
| 4,029,696 | 6/1977 | Sommer et al. | 260/429 J |

FOREIGN PATENT DOCUMENTS

| | | | |
|---|---|---|---|
| 100609 | 3/1965 | Denmark | 260/429 J |
| 1110822 | 7/1961 | Fed. Rep. of Germany | 424/5 |
| 238543 | 3/1926 | United Kingdom | 260/429 J |
| 1493974 | 12/1977 | United Kingdom | 424/4 |

OTHER PUBLICATIONS

Investigative Radiology, vol. 3, 229–238, (1968), Nadel et al.
Sawyer–Chem. Rev. 64, 6 (1964), pp. 633–643.
Brnicevic et al.–Journal of the Less–Common Metals, 23 (1971), 61–65.
Chem. Abstracts, vol. 61 (1964), 864f.

*Primary Examiner*—Frederick E. Waddell
*Attorney, Agent, or Firm*—Jon S. Saxe; George M. Gould; R. Hain Swope

[57] ABSTRACT

Radiographic contrast media preparations suitable for use with high-energy x-ray sources and useful for intestinal tract studies and, in particular, computerized tomography are disclosed. The disclosed preparations comprise aqueous solutions of stable, non-toxic complexes of hafnium and tantalum with certain organic acids.

6 Claims, No Drawings

RADIOGRAPHIC COMPOSITIONS

BACKGROUND OF THE INVENTION

Computerized tomography (CT), also known as computerized transaxial tomography, is recognized as a major breakthrough in x-ray technology. Sales of the equipment necessary to perform CT scans have risen sharply each year since their introduction in 1972. CT scans, by combining and integrating thousands of x-ray images simultaneously taken from a number of different angles around the body, produce cross-sectional images or "slices" of the body. The use of CT scans greatly improves density resolution of the resultant image over conventional x-rays, and, more importantly, it overcomes the problem of superimposition always inherent in a two-dimensional representation of a three-dimensional object.

One problem which has become apparent during the rapid development of CT scanning apparatus is that the contrast media preparations commercially available are not ideally suited for use therewith for several reasons. First, CT procedures utilize a high-energy x-ray source, i.e. peak energy levels in the 120–150 keV range and mean energy in the 50–80 keV range. Therefore, contrast preparations utilized in such procedures should ideally have a K-absorption edge in the 50–80 keV range. The preparations currently in use, which are principally insoluble salts of barium and iodinated lipids are not ideally suited for CT scans since they have K-absorption edges in the 30–40 keV range.

A second major disadvantage with most commercial preparations insofar as their use in CT procedures is concerned is their behavior in the intestinal tract. For example, the barium sulfate preparations present the pharmaceutical chemist a problem in obtaining uniform and stable suspensions of the highly insoluble barium salts which must be employed to avoid the toxicity of soluble barium preparations. Consequently the ability of radiographic preparations containing $BaSO_4$ to achieve outlining of the bowel is dependent on the capability of suspending agents to cause the insoluble particulate material to adhere to the bowel wall. This problem is even more pronounced with certain barium sulfate preparations which have a tendency to agglomerate. This tendency materially detracts from their ability to uniformly coat the gastrointestinal tract.

The organic iodinated lipid preparations commercially utilized as contrast media are advantageous over the barium sulfate preparations in that they form homogeneous solutions. However, the iodine preparations have an even lower K-absorption edge than barium sulfate, a disadvantage in their use with the high-energy x-rays employed in CT studies. In addition, many iodine-containing preparations increase intestinal motility. This markedly detracts from the capability of such preparations to coat the intestinal mucosa and increases the rate at which they pass through the bowel. In addition, the increased intestinal motility caused by such preparations tends to form regional localized "puddling" in the intestinal tract lumen. Rapid passage of a contrast material through the bowel can be a distinct disadvantage for radiographic preparations since such preparations would only permit visualization of each segment of the bowel during only a short period of time.

In contrast to the aforementioned commercially available materials, preparations are realized in accordance with the present invention which, in addition to being stable and non-toxic, form aqueous solutions which are stable over the pH range encountered within the gastrointestinal tract and uniformly coat the intestinal mucosa, are uniformly distributed throughout the intestinal tract, do not increase intestinal motility and, most important, have a high K-absorption edge therefore being well suited for studies employing high-energy x-ray beams such as those used in CT studies.

STATEMENT OF PRIOR ART

The following references are pertinent to the subject invention.

Dure-Smith et al U.S. Pat. No. 3,937,800 which discloses a composition suitable for bronchography comprising finely divided tantalum and a metallic soap in an oily vehicle.

Llamas et al, Dis Chest 56 (1), pp 75–77, July 1969 describes the use of pure, finely divided tantalum powder by insufflation for bronchograpy.

Nadel et al, Invest Radio 4 (2), pp 57–62, March-April 1969 and Stewart et al, Radiology 93 (1), pp 176–177, July 1969 describe the use of finely divided tantalum powder in insufflation esophagoscopy.

Finally, Yoshida Japanese Patent publication No. 2891/64 dated Mar. 9, 1964 discloses radiographic preparations comprising homogeneous suspensions containing barium sulfate and less than 10% by weight based on the weight of the barium sulfate, of calcium tungstate.

None of these references teaches or suggests the soluble hafnium or tantalum complexes of the subject invention or the use of such complexes as enteric radiographic agents, particularly for CT scans.

DETAILED DESCRIPTION OF THE INVENTION

The present invention is directed to novel radiographic preparations useful in intestinal tract studies and particularly suited to computerized tomography (CT) studies. The subject preparations are especially useful in such studies because they have a high K-absorption edge which approximates the high average energy typically utilized in CT studies. It is recognized by those skilled in the art that the use of high-energy x-rays for contrast studies in the body results in a decrease in the radiation dose absorbed by the body relative to the amount of information-bearing x-rays which reach the radiation detector system. It is likewise recognized in the art that, if the K-absorption edge of the contrast media utilized approximates that of the level of x-ray mean energy being utilized, greater definition of the contrast agent is obtained.

In CT studies of the abdomen, bowel structures must be distinguished from other structures, e.g. the pancreas, kidneys, tumors, tumors involving mesenteric lymph nodes, other mesenteric structures and the like. It is also important in this regard that the bowel be substantially coated with contrast agent so that bowel loops can be distinguished from other structures as mentioned above. The preparations of the subject invention are ideally suited for CT studies because they possess both a high K-absorption edge and the ability to coat the intestinal mucosa.

The preparations of the present invention comprise aqueous solutions of soluble, non-toxic hydrated complexes of tantalum or hafnium with a chelating or complexing agent selected from the group consisting of: (1) organic acids, having between 2 and 7 carbon atoms and at least one hydroxyl group such as, for example, gluconic acid, glyceric acid, glucuronic acid, ascorbic acid, erythorbic acid, tartaric acid, citric acid and the like; (2) amino acids, containing 2 to 8 carbon atoms preferably α-amino acids such as serine, glycine, methionine, threonine and the like; and (3) a phosphonic acid selected from the group consisting of ethylenediaminetetramethylenephosphonic acid, diethylenepentamethylenephosphonic acid, and diphosphonates represented by the formula

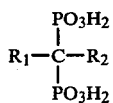

wherein $R_1$ and $R_2$ may be the same or different and are selected from the group consisting of hydrogen, lower alkyl, amino, halogen, hydroxyl, and —$CH_2$-COOH. Preferred phosphonic acids in accordance with the invention are ethane-1-hydroxy-1,1-diphosphonic acid, methane diphosphonic acid, ethylenediaminetetramethylenephosphonic acid, and diethylenepentamethylenephosphonic acid.

The selection of a member of the above-mentioned groups of complexing agents must be made with certain criteria in mind. The most important is that the complex formed between such agent and tantalum or hafnium must be water-soluble. Those complexes which are not water-soluble cannot be utilized in the practice of the present invention. By water-soluble is meant that a given complex must be capable of completely dissolving in water at a concentration of at least 2% weight to volume of the metal contained in the complex. Although solutions containing 1% weight-to-volume metal can be visualized in the gut, such solutions are considered too dilute to give an acceptable radiographic study. The minimum of 2% W/V of the metal, which is typically 5% to 6% W/V of the complex, depending on which complexing agent is utilized, is for CT scans. Most common radiographic studies other than CT studies require higher concentration of radiographic agents.

Second, the complexing agent selected for the practice of the invention must be a sufficiently strong chelating agent to prevent the formation of the insoluble hydroxides of hafnium or tantalum which will precipitate from solution and reduce the effectiveness of the radiographic preparation. The chelates formed with the above-named complexing agents and either tantalum or hafnium must additionally be stable and remain in solution over the pH range of the human gastrointestinal tract, i.e. a pH range of from about 1.5 in the stomach to about 9.2 in the duodenum.

The complexes of the present invention are prepared by initially forming a solution of a soluble salt of either hafnium or tantalum such as, for example, the chloride, oxychloride, fluoride, iodide or bromide. In the case of hafnium, the solutions of the above-mentioned salts may be in water or a suitable organic solvent. In the case of tantalum, however, the initial solution must be in a suitable organic solvent, preferably a lower alkanol, most preferably methanol or ethanol. To this solution is added a concentrated solution of the desired chelating agent, preferably but not necessarily in the solvent utilized to dissolve the salt. Since the above solutions are very acidic, the pH of the reaction mixture at this point is about 1.5 to 3.

The neutral, buffered salt of the hydrated complexed metal obtained as described above is formed by the addition to an aqueous or aqueous/alcoholic solution of the complex of a sufficient quantity of an aqueous solution of a pharmaceutically acceptable base as will be discussed hereinafter.

Wherein the salts of the hydrated, complexed metals are formed in aqueous medium, they are recovered in purified form by a unique method. Initially, the salt is precipitated from solution by the addition of a large excess of methanol. Contaminating salts, initially coprecipitated with the complex, are removed by heating the mixture to about 60° C. and subsequently removing the precipitated complex either by filtration or by decanting the methanol. The desired complex is then further purified by washings with hot methanol.

The hydrated complex or a salt thereof with a pharmaceutically acceptable base may be further dried by heat or by use of dehydrating solvents. The dry, stable complex is then packaged to be used at a later time simply by dissolving in sufficient water to form a solution having the desired concentration.

The complexes of the present invention are named as the hydrated chelated metal or its salt with a pharmaceutically acceptable base. Since the cation of the base is considered part of the complex, it is so-named, i.e. as a total complex, for example, hydrated hafnium-ammonium-gluconate. In actuality, the waters of hydration typically undergo hydrolysis and the dihydroxy form predominates in aqueous solution after the pH of the complex is raised by addition of base from the acidic level at which it is formed to, in essence, neutrality. Further, as stated above, the complex acquires cations from the base utilized to adjust the pH, i.e. ammonium, sodium or potassium hydroxide, respectively. Although the exact structure of the complexes of the invention is not known, the nomenclature thereof is in agreement with the empirical formulae determined therefor. For example, the empirical formula of hydrated hafnium-ammonium-gluconate determined by elemental analysis is $(HfO)_2(NH_4)_2gluconate_3 \cdot (H_2O)_x$.

The complexes of the present invention are formed utilizing an amount of the acid complexing agent in excess over the stoichiometric requirement. The amount in excess is of no consequence, for practical purposes. Generally, an excess of from about 1 molar part to about 4 molar parts of acid complexing agent are utilized for each molar part of the metal to be complexed. The excess complexing agent is removed simply by precipitating the complex with a solvent in which the complexing agent is soluble or miscible and subsequently washing the precipitated complex with the solvent.

The salts formed by bringing the complexes of the present invention to neutrality are salts with pharmaceutically acceptable monovalent bases such as, for example, ammonium, sodium or potassium hydroxide. Since the cation of the base will affect the solubility of the complex, the choice of the pharmaceutically acceptable base for the neutralization step is critical. Of the salts given above, ammonium hydroxide is preferred first because it is a weak base and second because its use does not result in the patient receiving a large quantity of fixed cations as in the case with sodium and potassium. Where the administration of a large quantity of fixed cations is acceptable in the clinical situation and, more importantly, where a complex meeting the required solubility is obtained, sodium or potassium may be used.

The radiographic complexes of the present invention are non-toxic upon oral administration. The methods of detection available indicate absorption to be less than $10^{-4}$. In addition, the complexes of the present invention have demonstrated an excellent ability to coat the intestinal tract utilizing high-energy x-rays.

The complexes of the present invention are utilized in solutions containing from about 1% to about 25% weight to volume of the metal, i.e. hafnium or tantalum. For CT scans from about 3% to about 5% weight to volume of the metal is preferred. For conventional radiographic procedures, from about 10% to about 20% weight to volume is preferred. In all instances it is important that the solution approximates the normal molarity of the gut, i.e. 270–290 mOsm. For example, a 12.5% weight to volume aqueous solution of hafnium ammonium gluconate is 280 mOsm. Wherein a solution having the desired concentration of the subject complexes is hypotonic, it is useful to add a sufficient amount of a compatible, pharmaceutically acceptable additive such as, for example, sodium chloride, to adjust the osmolarity of the preparation to that present in the gut.

The complexes of the subject form aqueous solutions which demonstrate good shelf life, i.e. up to 6 months. The complexes of the invention may be packaged for commercial use either as aqueous solutions or, preferably, in dry form. The aqueous solutions are sterilized by conventional means to prevent bacterial growth. Although the inclusion of a pharmaceutically acceptable preservative in such solutions is within the scope of the invention, it is preferred to omit such preservatives in most instances.

As stated above, the complexes of the present invention containing tantalum must be formed in an organic solvent, e.g. methanol or ethanol. However, once such complexes are prepared and the pH adjustment carried out, the final complex is unexpectedly both soluble and stable in water.

The complexes of the present invention and the radiographic preparation containing them demonstrate excellent stability in the pH range of the gastrointestinal tract, are not absorbed and are non-toxic, remain in solution throughout passage throughout the gastrointestinal tract, possess exceptional ability to coat the intestinal mucosa and give clear resolution with high-energy x-rays.

The following examples further illustrate the invention. Unless otherwise indicated all temperatures are in degrees Centigrade.

EXAMPLE 1

Hydrated hafnium-ammonium-gluconate was prepared as follows: 125 grams of hafnium oxychloride.8-H$_2$O was dissolved in 600 ml of 50% aqueous solution gluconic acid. Four litters of anhydrous methanol were added to precipitate the hafnium-gluconate and the suspension was heated to 60° with stirring for 30 minutes. The pH of the preparation was then adjusted to 6.5 by addition of concentrated NH$_4$OH. The hot solution was filtered to remove NH$_4$Cl and ammonium gluconate. The precipitate was dried at 90° for 1 hour, resuspended in anhydrous methanol at 60° with stirring for 60 minutes then filtered to remove additional excess of NH$_4$Cl and ammonium-gluconate. The precipitate was further extracted to remove additional NH$_4$Cl and ammonium-gluconate employing anhydrous methanol in a Soxhlet apparatus, extraction was continued until the methanol surrounding the precipitate was clear. The precipitate was then dried at 90° for approximately 2 hours and ground to a fine powder. Elemental analysis was consistent with a formula of (HfO)$_2$(NH$_4$)$_2$ gluconate$_3$(H$_2$O)$_x$. It was found that the same final product was obtained when the molar ratio of gluconic acid to hafnium was varied from 1:1 to 100:1. Moreover, the same product was obtained utilizing hafnium-tetrachloride instead of hafnium-oxychloride.

The hydrated hafnium-ammonium-gluconate powder was freely soluble in water in concentrations up to 50% W/V. A 12.5% W/V solution was found to have an osmolarity of 280 mOsm and was stable without evidence of precipitation over a pH range of 1 to 12. Solutions of 20% and 25% W/V were administered to dogs and rats in performance of intestinal radiography which provided good X-ray contrast. No evidence of increased intestinal motility caused by the agent was noted. Eighty ml of a 7.5% W/V solution of hydrated hafnium-ammonium-gluconate was administered orally to dogs and computerized tomography of the abdomen was performed for time periods up to 24 hours following such administration. In a comparative test with the commercial iodinated lipid Diatrizoate Meglumine, the 7.5% W/V solution of hydrated hafnium-ammonium-gluconate demonstrated both a slower intestinal transit and a more uniform distribution of the agent throughout the bowel.

Toxicity of hydrated hafnium-ammonium-gluconate was studied in rats given 2 ml of a 12.5% W/V solution orally each day for 21 days. No differences were noted between rats given such administration and those given comparable quantities of 5% glucose in water. Systematic absorption was studied in rats following oral administration of [181]Hf-labeled hydrated hafnium-ammonium-gluconate and found to be less than $10^{-4}$.

EXAMPLE 2

Hydrated hafnium-sodium-glycerate was prepared as follows: 1.8 grams of hafnium-oxychloride.8H$_2$O were dissolved in 1.8 ml of 65% W/V mixture of glyceric acid and water and the pH adjusted to 6.5 by addition of NaHCO$_3$. Hydrated hafnium-sodium-glycerate was precipitated by the addition of 100 ml of anhydrous methanol. The precipitate was filtered and dried at 90°. Elemental analysis showed that the product contained 35.6% hafnium. The product was labeled with [181]Hf and its distribution following oral administration to rats was studied. Results were comparable to those obtained with [181]Hf-labeled hydrated hafnium-ammonium-gluconate prepared in Example 1. The material was stable in aqueous solution over a pH range of 1 to 12. Aqueous solutions of hydrated hafnium-sodium-glycerate in concentrations up to 20% W/V were prepared and found to be stable. Two ml portions of a 1 M aqueous solution were administered orally to rats and serial radiographs were obtained which showed good contrast with uniform distribution comparable with the results obtained in Example 1 with hydrated hafnium-ammonium-gluconate.

EXAMPLE 3

Hydrated hafnium-sodium-citrate was prepared as follows: 1.5 grams of hafnium-oxychloride and 1.05 grams of citric acid crystals were dissolved in 5 ml of water. The pH was adjusted to 6.5 with sodium hudroxide. The resulting aqueous preparation of hydrated hafnium-sodium-citrate was concentrated by evaporation in vacuum to a 1 molar concentration. Two ml portions of a 1 M solution was administered orally to rats and serial radiographs were obtained which showed good contrast with uniform distribution comparable to those obtained in Examples 1 and 2. Water-soluble hydrated hafnium-ammonium-citrate complexes were similarly obtained utilizing citrate-to-hafnium in molar ratios of between 0.75:1 and 5.0:1. In a like manner, hydrated hafnium-ammonium-citrate was obtained utilizing ammonium-hydroxide to adjust the pH.

EXAMPLE 4

Hydrated hafnium-ammonium-ascorbate was prepared as follows: 1.6 grams of hafnium-tetrachloride and 1.86 grams of crystalline ascorbic acid were dissolved in 5 ml of water, and the pH was adjusted to 6.5 with ammonium hydroxide. Two ml portions of the resulting solution were administered orally to rats and radiographs were obtained comparable to those seen with preparations described in the previous examples. Soluble complexes of ascorbic acid and hafnium possessing similar properties were obtained using molar ratios of ascorbic acid to hafnium of from 1:1 to 4:1.

EXAMPLE 5

Complexes of hafnium were prepared with several amino acids as follows. The hafnium-chloride, i.e. both the oxychloride and the tetrachloride were utilized alternately, was dissolved in an aqueous solution of each of the amino acids and the pH adjusted to 6.5 as in previous examples. The following amino acids were used: threonine in a ratio to hafnium of 2:1, methionine, serine and glycine individually in ratios to hafnium of 2:1, 3:1 and 4:1, respectively. The thus-formed hydrated hafnium-amino acid complexes were administered orally to rats and serial radiographs were obtained which were comparable to those obtained with the preparations described in the previous examples.

EXAMPLE 6

Hydrated tantalum-sodium-citrate was prepared as follows: 1.5 grams of tantalum-pentachloride were added to 3.0 grams crystalline citric acid dissolved in 10 ml of anhydrous methanol and the mixture evaporated to dryness at 50° under vacuum. The precipitate was washed three times with anhydrous methanol. Two grams of the dry precipitate were dissolved in 10 ml of water and the pH adjusted to 6.0 by addition of NaOH. The solution was filtered through 22μ filter and the filtrate administered orally to rats. Radiographs were then obtained which were comparable to those obtained with the preparations described in the previous examples.

EXAMPLE 7

Hydrated tantalum-sodium-tartrate was prepared as follows utilizing, individually, D-tartaric acid, L-tartaric acid, D,L-tartaric acid, and mesotartaric acid. In each instance, the complex was prepared by adding 1.7 grams tantalum-pentachloride to 2.0 grams of the tartaric acid dissolved in 10 ml methanol. The various tartaric acids behaved similarly. The alcoholic solution was dried under vacuum and the precipitate washed three times with anhydrous methanol. The dried precipitate was dissolved in 10 ml water and the pH adjusted to 6.5 using $NaHCO_3$. Acceptable complexes were prepared by varying the molar ratio of tartaric acid to tantalum from 2:1 up to 6:1. The complexes of this example formed stable aqueous solutions in concentrations up to 2 molar. Two ml samples of aqueous solutions containing the complexes formed in this example at concentrations of 18% to 20% W/V were administered orally to rats. Radiographs were thereafter obtained which were comparable to those of the previous examples.

EXAMPLE 8

The tantalum complex of ethane-1-hydroxy-1,1-diphosphonic acid was prepared as follows: 1.8 grams of tantalum-pentachloride were dissolved in 4.4 ml of anhydrous methanol and 1.6 ml of a 60% W/V aqueous solution of ethane-1-hydroxy-1,1-diphosphonic acid were added thereto. The solution was evaporated to dryness under vacuum. The precipitate was washed three times with anhydrous methanol and the dry precipitate dissolved in 6 ml water. The pH was adjusted to 6.5 by addition of $NaHCO_3$. Acceptable complexes were obtained by varying the molar ratio of ethane-1-hydroxy-1,1-diphosphonic acid to tantalum from 1:1 up to 5:1. Two ml samples of aqueous solutions of the complexes of this example in various concentrations up to 1 molar were orally administered to rats. The radiographs thereafter obtained were comparable to those obtained with the preparations of the previous examples.

We claim:

1. A method of preparing a patient for radiographic examination of the gastrointestinal tract which comprises orally administering to said patient an amount of a composition comprising an aqueous solution of a stable, non-toxic, hydrated complex of a metal selected from the group consisting of hafnium and tantalum and an organic acid complexing agent selected from the group consisting of:
   (a) an organic acid containing from 2 to 7 carbon atoms and at least one hydroxyl group;
   (b) an amino acid containing from 2 to 7 carbon atoms: and
   (c) a phosphonic acid selected from the group consisting of ethylenediaminetetramethylenephosphonic acid, diethylenepentamethylenephosphonic acid and diphosphonic acids represented by the formula

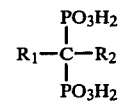

wherein $R_1$ and $R_2$ are the same or different and are selected from the group consisting of hydrogen, lower alkyl, amino, halogen, hydroxyl and —$CH_2$—COOH and pharmaceutically acceptable salts thereof, said salts being selected from the group consisting of the ammonium salt, the sodium salt and the potassium salt, said composition containing from about 1% to about 25% weight to volume of said metal, effective for said examination.

2. A method of preparing a patient in accordance with claim 1 wherein said metal is hafnium and said organic acid complexing agent is selected from those acids in groups (a) and (b).

3. A method of preparing a patient in accordance with claim 2 wherein said organic acid complexing agent is selected from the group consisting of gluconic acid, glyceric acid, citric and ascorbic acid.

4. A method of preparing a patient in accordance with claim 3 wherein said complex is hydrated hafnium-ammonium-gluconate.

5. A method of preparing a patient in accordance with claim 1 wherein said metal is tantalum and said organic acid complexing agent is selected from those acids in groups (a) and (c).

6. A method of preparing a patient in accordance with claim 5 wherein said organic acid complexing agent is selected from the group consisting of citric acid, tartaric acid and ethane-1-hydroxy-1,1-diphosphonic acid.

* * * * *